(12) United States Patent
Wang et al.

(10) Patent No.: US 11,624,273 B2
(45) Date of Patent: Apr. 11, 2023

(54) SHALE OIL FRACTURING SYNCHRONOUS ENERGIZING SIMULATION EXPERIMENTAL DEVICE AND METHOD

(71) Applicant: China University of Petroleum (East China), Qingdao (CN)

(72) Inventors: Sen Wang, Qingdao (CN); Qihong Feng, Qingdao (CN); Yichun Wang, Qingdao (CN); Xianmin Zhang, Qingdao (CN); Jiyuan Zhang, Qingdao (CN); Xian Shi, Qingdao (CN)

(73) Assignee: China University of Petroleum (East China), Qingdao (CN)

( * ) Notice: Subject to any disclaimer, the term of this patent is extended or adjusted under 35 U.S.C. 154(b) by 0 days.

(21) Appl. No.: 17/654,546

(22) Filed: Mar. 11, 2022

(65) Prior Publication Data

US 2022/0298902 A1    Sep. 22, 2022

(30) Foreign Application Priority Data

Mar. 16, 2021   (CN) .......................... 202110280972.0

(51) Int. Cl.
*G01N 33/24* (2006.01)
*E21B 43/26* (2006.01)
(Continued)

(52) U.S. Cl.
CPC .............. *E21B 43/26* (2013.01); *E21B 47/06* (2013.01); *E21B 49/087* (2013.01); *G01N 33/24* (2013.01)

(58) Field of Classification Search
CPC ...... E21B 43/26; E21B 41/00; E21B 41/0092; E21B 2200/20; G01N 33/24; G01N 15/0806; G01V 15/082
See application file for complete search history.

(56) References Cited

U.S. PATENT DOCUMENTS

| 9,921,202 B2 * | 3/2018 | Huang | ..................... G01L 15/00 |
| 10,712,253 B2 * | 7/2020 | Su | ....................... G01N 15/0806 |

(Continued)

FOREIGN PATENT DOCUMENTS

| CN | 105952429 | 9/2016 |
| CN | 109025939 | 12/2018 |

(Continued)

OTHER PUBLICATIONS

Chinese Patent Application No. 202110280972.0, Notification to Grant Patent Right for Invention, dated Sep. 6, 2022, 2 pages.

(Continued)

*Primary Examiner* — Kenneth L Thompson
(74) *Attorney, Agent, or Firm* — DLA Piper LLP (US)

(57) ABSTRACT

The present disclosure relates to the technical field of oil-gas field development, and discloses a shale oil fracturing synchronous energizing simulation experimental device and method. The shale oil fracturing synchronous energizing simulation experimental device comprises a liquid supply system, a confining pressure loading system, a fracturing system, an energizing system and a recovery system, wherein the liquid supply system is used for storing fluid and can inject the fluid into the fracturing system; the fracturing system can bear a test piece, receive the fluid injected by the liquid supply system and serve as seepage space of the fluid; the confining pressure loading system is used for providing simulated confining pressure for the test piece; the energizing system is used for simulating an energizing effect on a test piece after fracturing liquid is injected; and the recovery system is used for collecting discharged liquid and separating and metering the discharged liquid.

16 Claims, 6 Drawing Sheets

(51) Int. Cl.
   *E21B 47/06*    (2012.01)
   *E21B 49/08*    (2006.01)

(56) References Cited

U.S. PATENT DOCUMENTS 10,845,291 B2 *  11/2020  Kanj ................. G01N 15/0826
11,054,405 B2 *   7/2021  Hu ........................ G01N 3/10
11,313,775 B2 *   4/2022  Li ........................ G01N 3/062

FOREIGN PATENT DOCUMENTS

| CN | 109113692 | 1/2019 |
| CN | 109856030 | 6/2019 |
| CN | 110208105 | 9/2019 |
| CN | 112459760 | 3/2021 |

OTHER PUBLICATIONS

Chinese Patent Application No. 202110280972.0, First Office Action, dated Jan. 24, 2022, 24 pages.

* cited by examiner

SHALE OIL FRACTURING SYNCHRONOUS ENERGIZING SIMULATION EXPERIMENTAL DEVICE AND METHOD

CROSS REFERENCE TO RELATED APPLICATION(S)

This application claims priority to Chinese Application No. 202110280972.0, filed on Mar. 16, 2021, the content of which is incorporated herein by reference in its entirety.

TECHNICAL FIELD

The present disclosure relates to the technical field of oil-gas field development, and specifically relates to a shale oil fracturing synchronous energizing simulation experimental device and method.

BACKGROUND ART

In recent years, shale (tight) oil reservoirs have become an important area of unconventional oil and gas development. As the main body of the storage space of the shale oil reservoir is a micro-nano pore-fracture system and the permeability is extremely low, the improvement on the seepage capacity of the reservoir by adopting a hydraulic fracturing technology becomes an effective way for developing the shale oil reservoirs. In the hydraulic fracturing process, tens of thousands of cubic meters of fracturing liquid is injected into the formation to form a complex artificial fracture network, and therefore the purpose of reservoir stimulation is achieved. After hydraulic fracturing, the well always undergo month-long shut-in times prior to the production, during which the fracturing liquid in a reservoir and crude oil are fully replaced, and meanwhile, the injected fracturing liquid has high pressure, so that energy can be supplemented to the formation; and then the oil well starts production in a depletion exploitation mode, and the recovery efficiency of the oil reservoir can be further improved by injecting a chemical agent for huff and puff and other modes in the subsequent process. Reasonable injection parameters of the fracturing liquid can achieve the fracturing synchronous energizing effect, so that the development effect of the shale (tight) oil reservoirs is effectively improved. Therefore, integrated simulation of fracturing synchronous energization and the subsequent production process is of great significance in clarifying the internal mechanism of the technology and improving the development effect of shale (tight) oil reservoirs.

CN109113692A discloses a matrix-fracture dual-medium huff-n-puff physical simulation device and a method for evaluating the recovery efficiency in the huff and puff process. The physical simulation device comprises an injection system, a matrix-fracture dual-medium system, a constant-pressure boundary system, a recovery system and a pressure monitoring system. The seepage process of low-permeability and tight reservoir matrix-fracture dual media, and the actual performance of field huff and puff can be well simulated.

CN109025939A provides an ultrasonic tight oil imbibition experimental device. The device comprises a rock fixing box, a fracturing pipe capable of being arranged in a tight oil-containing rock in a penetrating mode is arranged on one side of the rock fixing box in a sealing and penetrating mode, the other end of the fracturing pipe is connected with a fracturing liquid injection structure in an openable and closable mode, a pushing structure is arranged in the fracturing pipe in a sealing, sliding and penetrating mode, and a plurality of ultrasonic probes are arranged on the pushing structure; and the side wall, penetrating through the fracturing pipe, of the rock fixing box is set as a first fixed box side wall, and a telescopic potential resistance imbibition test structure is arranged on each side wall, adjacent to the first fixed box side wall, of the rock fixing box. The ultrasonic tight oil imbibition experimental device further comprises a control part, and the control part can control the working states of the fracturing liquid injection structure, the pushing structure and the potential resistance imbibition test structure.

CN109856030A provides an imbibition experimental device and a determination method of imbibition recovery. The experimental device comprises an imbibition bottle, a micro-pressure pump and a hanging bracket, wherein water and a core sample are contained in the imbibition bottle, the imbibition bottle is provided with an opening end, a test tube is arranged at the opening end, scale marks are marked on the test tube from the upper end to the lower end, and the water level in the imbibition bottle is not lower than the scale mark at the lowermost end of the test tube; the micro-pressure pump is used for providing water with preset pressure into the imbibition bottle; the hanging bracket is used for hanging the core sample and placed on a gravity sensor, and the gravity sensor is electrically connected with a data acquisition system; wherein the imbibition bottle is provided with a water inlet, the water inlet is connected with the micro-pressure pump through a connecting device, and the connecting device comprises a hydraulic control valve which is in an open state when the hydraulic control valve detects that the pressures on the two sides are not equal; and when the hydraulic control valve detects that the pressures on the two sides are equal, the hydraulic control valve is in a closed state.

CN110208105A discloses a triaxial coal rock multi-field multiphase coupling fracturing experimental device and method. The experimental device comprises a gas-liquid coupling solution supply system, a stress loading system, a temperature control system, a recovery system and a fracturing process monitoring system, wherein the gas-liquid coupling solution supply system comprises a gas supply pipeline, a liquid supply pipeline and a gas-liquid mixing device, and the gas supply pipeline and the liquid supply pipeline are connected with a gas inlet and a liquid inlet of the gas-liquid mixing device, respectively.

Current experimental devices and methods for shale oil hydraulic fracturing and exploitation have the following problems:

Firstly, the hydraulic fracturing device can simulate a traditional fracturing process, but the energy carried by redundant fracturing liquid in the fracturing process needs to be stored due to fracturing synchronous energization effect so as to meet the requirement for energy supplement in the subsequent production process, and an existing hydraulic fracturing experimental device cannot simulate the process.

Secondly, the current shale oil exploitation experimental devices cannot realize integrated simulation of fracturing and exploitation; and in an exploitation experiment, cracks on the core sample are not obtained through actual fracturing, but are obtained through manual wire cutting or splicing, and the complex fracturing network in an actual reservoir cannot be taken into account.

Therefore, an experimental device and method capable of integrally simulating shale oil fracturing synchronous energization and subsequent exploitation processes (depletion and oil recovery agent huff-n-puff) are urgently required.

SUMMARY

The present disclosure aims to solve the problem that in the prior art, no experimental device capable of integrally simulating shale oil fracturing synchronous energization and subsequent exploitation processes (depletion and oil recovery agent huff and puff) exists, and provides a shale oil fracturing synchronous energizing simulation experimental device.

In order to achieve the above purpose, in the first aspect, the present disclosure provides a shale oil fracturing synchronous energizing simulation experimental device. The shale oil fracturing synchronous energizing simulation experimental device comprises a liquid supply system, a confining pressure loading system, a fracturing system, an energizing system and a recovery system, wherein the liquid supply system is used for storing fluid and can inject the fluid into the fracturing system; the fracturing system can bear a test piece, the fracturing system is used for simulating the rock medium of a tight reservoir and boundary conditions around the rock medium, receives the fluid injected by the liquid supply system and serves as a seepage space of the fluid, and the fracturing system is configured to be capable of maintaining own temperature; the confining pressure loading system is connected with the fracturing system and used for providing simulated confining pressure for the test piece, and the confining pressure loading system can maintain stable stress conditions in the horizontal and vertical directions for the test piece; the energizing system is connected with the fracturing system and used for simulating an energy supplementing effect on the test piece after fracturing liquid is injected; and the recovery system is used for collecting liquid discharged from the fracturing system, and the recovery system can control the production pressure of the fracturing system and separate and meter the discharged liquid.

By utilizing the experimental device provided by the present disclosure, integrated simulation of shale oil fracturing and exploitation can be realized, fracturing synchronous energization and simulation of subsequent reservoir depletion and oil recovery agent huff-n-puff are realized through the same set of experimental device, and the recovery efficiencies of different exploitation modes are evaluated. Fractures on a sample used for the simulation of the exploitation process are obtained by actual fracturing instead of being manually set, so that the actual conditions of a reservoir can be simulated more accurately, and effective means is provided for the studies on the fracturing synchronous energizing mechanism and the enhanced recovery technologies of an unconventional oil reservoir; and in addition, by utilizing the experimental device provided by the present disclosure, the fracturing synchronous energizing process of the shale oil under a real reservoir condition can be simulated. In the fracturing process, redundant energy of fracturing liquid is stored through the energizing system and released in the subsequent production process, the pressure attenuation speed of the test piece is reduced, and the fracturing synchronous energizing effect is effectively embodied.

Preferably, the liquid supply system comprises a plurality of liquid storage containers, the liquid storage containers are respectively used for storing different types of fluids, and the fluids in the liquid storage containers communicate with the fracturing system.

Preferably, at least one of the liquid storage containers is configured to be capable of controlling the internal pressure of the liquid storage container, and a flow meter is arranged on a pipeline between the liquid supply system and the fracturing system.

Preferably, the fracturing system comprises movable loading plates, the loading plates are arranged around the test piece, and the confining pressure loading system is connected with the loading plates so as to provide confining pressure for the test piece.

Preferably, the confining pressure loading system comprises a large true triaxial loading servo supercharger, a true triaxial loading instrument hydraulic source and a true triaxial loading instrument controller, the true triaxial loading instrument hydraulic source is in fluid connection with the large true triaxial loading servo supercharger so as to provide a hydraulic source for the large true triaxial loading servo supercharger, the true triaxial loading instrument controller is connected with the large true triaxial loading servo supercharger, and the large true triaxial loading servo supercharger is connected with the loading plates so as to provide confining pressure for the test piece.

Preferably, the test piece is a core sample for a shale oil reservoir, and the shale core is arranged in the fracturing system so as to simulate a shale medium of a shale oil reservoir and boundary conditions around the shale medium of the shale oil reservoir.

Preferably, the fracturing system comprises warmers and acoustic emission probes, the warmers are connected with the test piece so as to control the temperature of the test piece, and the acoustic emission probes are arranged around the test piece so as to monitor the damage condition of the test piece.

Preferably, the energizing system comprises a high-pressure energy storage tank, the high-pressure energy storage tank is filled with a constant-pressure medium located on the upper portion and an energizing fluid located on the lower portion, and the lower portion of the high-pressure energy storage tank is connected with the fracturing system so as to simulate an energizing effect after fracturing liquid is injected.

Preferably, the recovery system comprises a back pressure valve, a back pressure pump, a buffer tank and an oil-water separation device, the back pressure valve is connected with the output end of the fracturing system, and the oil-water separation meter is connected with the back pressure valve so as to collect, separate and meter liquid extracted from the fracturing system; and the back pressure pump is connected with the back pressure valve through the buffer tank so as to control bottom hole pressure in the production process.

In the second aspect, the present disclosure provides a shale oil fracturing synchronous energizing simulation experimental method, wherein the method uses the shale oil fracturing synchronous energizing simulation experimental device, and the method comprises the following steps: a preparation stage: injecting crude oil into the test piece in a fracturing system so that the internal pressure of the fracturing system reaches a preset pressure P1, and recording the volume V1 of the injected crude oil; heating a core sample for a shale oil reservoir for simulating a shale medium of a shale oil reservoir and boundary conditions around the shale medium of the shale oil reservoir to a preset temperature T1, and stabilizing the test piece for a period of time t1; a fracturing stage: injecting fracturing liquid into the fracturing system through a liquid supply system for a fracturing experiment in which the injection time of the fracturing liquid is t2, and metering the volume V2 of the injected fracturing liquid; a soak stage: starting the energizing system so as to maintain the pressure of the fracturing system at P1, maintaining the fracturing system at the temperature T1 so that the shale oil fracturing synchronous energizing simulation experimental device is stabilized for a period of time t3 and the crude oil and the fracturing liquid in the test piece form a mixed fluid; a recovery stage: controlling the pressure of the fracturing system to be P2 through the recovery system, and separating and metering the mixed fluid through the recovery system to obtain primary extracted crude oil and fracturing liquid; metering the volume V3 of the primary extracted crude oil and the volume V4 of the extracted fracturing liquid; and an oil recovery agent huff-n-puff stage: closing the recovery system, injecting an oil recovery agent into the fracturing system by utilizing the liquid supply system, performing oil recovery agent huff and puff so that the pressure in the fracturing system reaches P3 and the shale oil fracturing synchronous energizing simulation experimental device is stabilized for a period of time t4; opening the recovery system, reducing the pressure of the fracturing system to P4, and collecting liquid in the fracturing system to the recovery system; separating the extracted liquid through the recovery system to obtain secondary extracted crude oil and the oil recovery agent; and metering the volume V5 of the secondary extracted crude oil and the volume V6 of the oil recovery agent.

Preferably, the core sample for a shale oil reservoir is a cubic test piece, a wellhole installed in a borehole is provided with holes and used for simulating the perforation fracturing process in the real exploitation process, and the preparation stage of the core sample for a shale oil reservoir comprises the following preparation steps: in order to perform a fracturing synchronous energizing experiment, enabling the prepared core to be cubic test piece; after drilling the wellhole, performing a pre-heating experiment on the test piece, and measuring the time for well hole temperature to reach T1 through a temperature sensor to determine the heating time in the formal experiment process.

Preferably, P1 is greater than or equal to 20 MPa and less than or equal to 70 MPa, T1 is greater than or equal to 40° C. and less than or equal to 150° C., and t1 is greater than or equal to 15 days and less than or equal to 30 days; t2 is greater than or equal to 30 s and less than or equal to 900 s; t3 is greater than or equal to 3 days and less than or equal to 10 days; P2 and P4 are equal and are greater than or equal to 5 MPa and less than or equal to 20 MPa; and P3 is greater than or equal to 15 MPa and less than or equal to 50 MPa.

DESCRIPTION OF REFERENCE SIGNS IN ATTACHED FIGURES

Figure 1:
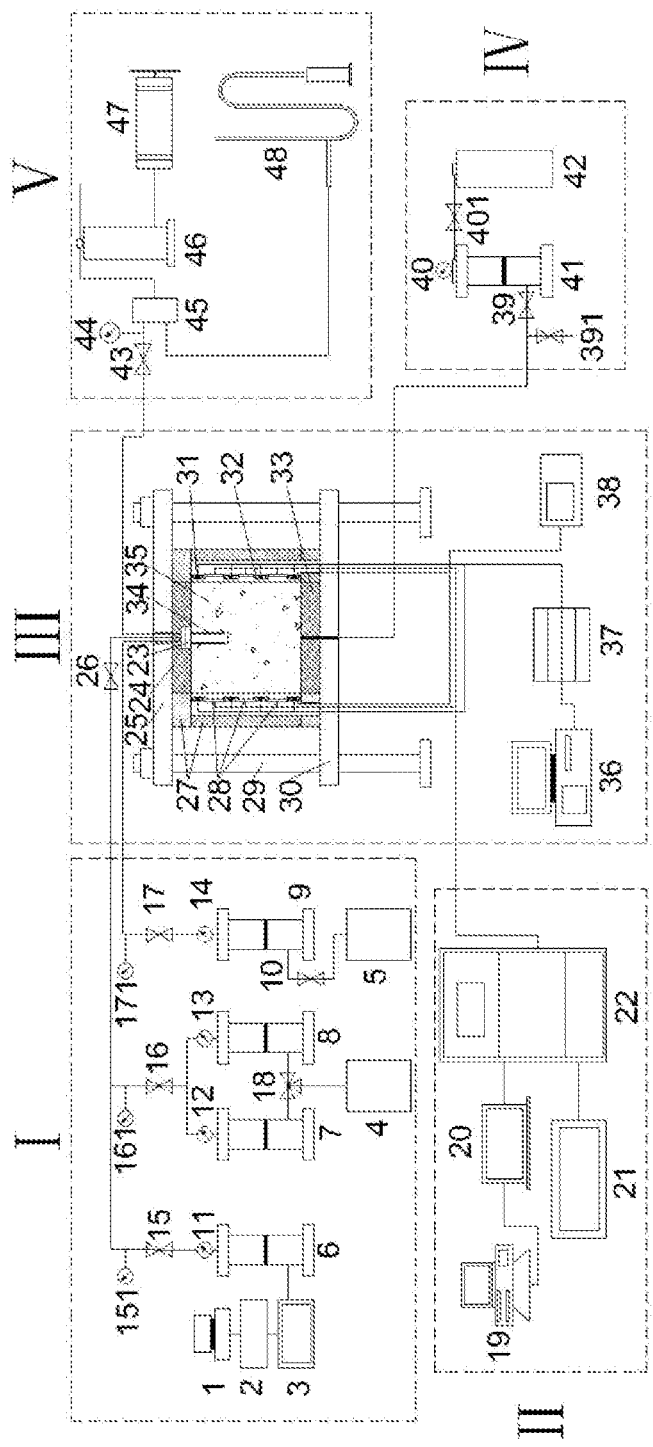
FIG. 1 is a structural schematic diagram of a shale oil fracturing synchronous energizing simulation experimental device provided by a preferred mode of execution of the present disclosure.

I, liquid supply system; II, confining pressure loading system;
III, fracturing system; IV, energizing system;
V, recovery system;
1, microcomputer (a); 2, pumping pressure system controller;
3, hydraulic source servo valve; 4, displacement pump (a);
5, displacement pump (b); 6, piston container (a);
7, piston container (b); 8, piston container (c);
9, piston container (d); 10, valve (a);
11, flow meter (a); 12, flow meter (b);
13, flow meter (c); 14, flow meter (d);
15, valve (b); 16, valve (c);
17, valve (d); 18, three-way valve;
19, microcomputer (b); 20, true triaxial loading instrument controller;
21, true triaxial loading instrument hydraulic source; 22, large true triaxial loading servo supercharger;
23, sealed wellhead; 24, upper pressing plate;
25, top cover; 26, valve (e);
27, sealing plate; 28, loading plate;
29, stabilizer; 30, base;
31, acoustic emission probe; 32, warmer;
33, lower pressing plate; 34, wellhole with holes;
35, test piece; 36, microcomputer (c);
37, differential preamplifier group; 38, temperature controller;
39, valve (0; 40, pressure meter (a);
41, high-pressure energy storage tank; 42, nitrogen cylinder;
43, valve (g); 44, pressure meter (b);
45, back pressure valve; 46, buffer tank;
47, back pressure pump; 48, oil-water separation meter;
49, pipeline (a); 50, pipeline (b);
51, pipeline (c); 52, pipeline (b);
53, pipeline (e); 54, pipeline (f);
55, pipeline (g); 151, precise pressure sensor (a);
161, precise pressure sensor (b); 171, precise pressure sensor (c);
281, fixator; 282, hydraulic piston;
283, pressure plate; 391, valve (h); and
401, valve (I).

DETAILED DESCRIPTION OF THE EMBODIMENTS

The following describes specific embodiments of the present disclosure with reference to the following attached figures. It shall be understood that, the embodiments described herein are only intended to illustrate and explain but not to limit the present disclosure.

The endpoints of the ranges and any value disclosed herein are not limited to the precise range or value, and these ranges or values should be understood to encompass values close to these ranges or values. Numerical ranges, between the endpoints of the respective ranges, between the endpoints of the respective ranges and the individual point values, and between the individual point values may be combined with one another to obtain one or more new numerical ranges, and these numerical ranges are to be considered as specifically disclosed herein.

In the present disclosure, the term "connection" includes both direct connection between two components and connection between two components through at least one intermediate component.

Liquid Supply System I

A liquid supply system I comprises four liquid storage containers which are a piston container (a) 6, a piston container (b) 7, a piston container (c) 8 and a piston container (d) 9.

Wherein, the piston container (a) 6 is used for containing fracturing liquid and is sequentially connected with a hydraulic source servo valve 3, a pumping pressure system controller 2 and a microcomputer (a) 1 to form a fracturing liquid supply pipeline; the upper end of the piston container (a) 6 is connected with a liquid inlet of a fracturing system III through a pipeline, and a flow meter (a) 11, a valve (b) 15 and a precise pressure sensor (a) 151 are arranged on the connecting pipeline and used for collecting and recording the total amount of pumped fracturing liquid and the pressure variation in the fracturing process.

The piston container (b) 7 is used for containing distilled water, and the piston container (c) 8 is used for containing a chemical agent solution; a displacement pump 4 is connected with the piston container (b) 7 and the piston container (c) 8, and the piston container (b) 7 and the piston container (c) 8 are connected with a liquid inlet pipe of the fracturing system III through pipelines and used for injecting an oil recovery agent into a test piece 35; a flow meter (b) 12, a flow meter (c) 13 and a precise pressure sensor (b) 161 are installed on a pipeline between the fracturing system III and the liquid storage tank and used for monitoring the volume of the injected oil recovery agent and the injection pressure variation. Wherein, the oil recovery agent can be pure water or a mixed solution of water and other chemical agents. Wherein, the chemical agent can be a surfactant solution, an inorganic salt solution, a particle suspension or a combined solution of different chemical agents, so that crude oil in core is displaced. In addition, due to the imbibition effect, a certain oil recovery is achieved, but the performance may be not ideal, and therefore some chemical agents such as surfactants can be added into the water to reduce the oil-water interfacial tension or change the reservoir wettability, and the oil can be extracted more easily.

The piston container (d) 9 is used for containing crude oil, the lower end of the piston container (d) 9 is connected with a displacement pump (b) 5 through a pipeline, and the upper end of the piston container (d) 9 is connected to an oil inlet pipe of the fracturing system III and used for injecting crude oil into a fracturing test piece to make the initial oil saturation; a valve (d) 17, a flow meter (d) 14 and a precise pressure sensor (c) 171 are installed on the pipeline between the fracturing system III and the piston container (d) 9 and used for monitoring the volume and the pressure of injected crude oil. Preferably, the fracturing test piece is vacuum saturated with crude oil.

Specifically, the liquid supply system I in the present disclosure is composed of a microcomputer (a) 1, a pumping pressure system controller 2, a hydraulic source servo valve 3, a displacement pump (a) 4, a displacement pump (b) 5, a piston container (a) 6, a piston container (b) 7, a piston container (c) 8, a piston container (d) 9, a valve (a) 10, a valve (b) 15, a valve (c) 16, a valve (d) 17, a three-way valve 18, a flow meter (a) 11, a flow meter (b) 12, a flow meter (c) 13, a flow meter (d) 14, a precise pressure sensor (a) 151, a precise pressure sensor (b) 161 and a precise pressure sensor (c) 171 which are connected through high pressure pipelines. The microcomputer (a) 1, the pumping pressure system controller 2, the hydraulic source servo valve 3, the piston container (a) 6, the flow meter (a) 11, the valve (b) 15 and the precise pressure sensor (a) 151 are sequentially connected to the liquid inlet pipe of the fracturing system III in series through high pressure pipelines. The displacement pump (a) 4, the piston container (b) 7 and the piston container (c) 8 are connected with the three-way valve 18 through high pressure pipelines, and the piston container (b) 7, the flow meter (b) 12, the piston container (c) 8 and the flow meter (c) 13 are connected to the liquid inlet pipe of the fracturing system III in parallel through high pressure pipelines. The valve (c) 16 is installed at an oil recovery agent injection pipeline. The displacement pump (b) 5, the valve (a) 10, the piston container (d) 9, the flow meter (d) 14, the valve (d) 17 and the precise pressure sensor (c) 171 are sequentially connected to the oil inlet pipe of the fracturing system III in series through high pressure pipelines.

Confining Pressure Loading System II

As shown in FIG. 1, in a preferred mode of execution of the present disclosure, the confining pressure loading system II comprises a large true triaxial loading servo supercharger 22, a true triaxial loading instrument hydraulic source 21 and a true triaxial loading instrument controller 20 and a microcomputer (b) 19; the large true triaxial loading servo supercharger 22 is respectively connected with the true triaxial loading instrument hydraulic source 21 and the true triaxial loading instrument controller 20; the microcomputer (b) 19 is connected with the true triaxial loading instrument controller 20, the large true triaxial loading servo supercharger 22 is connected with a fracturing system, and can apply confining pressure to a test piece 35 in the fracturing system by utilizing hydraulic pressure provided by the true triaxial loading instrument hydraulic source 21, simulate reservoir conditions, monitor stress states and maintain stress stability.

Specifically, the confining pressure loading system II is composed of a large true triaxial loading servo supercharger 22, a microcomputer (b) 19, a true triaxial loading instrument controller 20 and a true triaxial loading instrument hydraulic source 21. The true triaxial loading instrument hydraulic source 21 and the true triaxial loading instrument controller 20 are respectively connected with the large true triaxial loading servo supercharger 22. The microcomputer (b) 19 is connected to the true triaxial loading instrument controller 20 and used for monitoring and controlling confining pressure. The confining pressure loading system II is connected with a plurality of loading plates 28 in the fracturing system III through pipelines.

Fracturing System III

Figure 2:
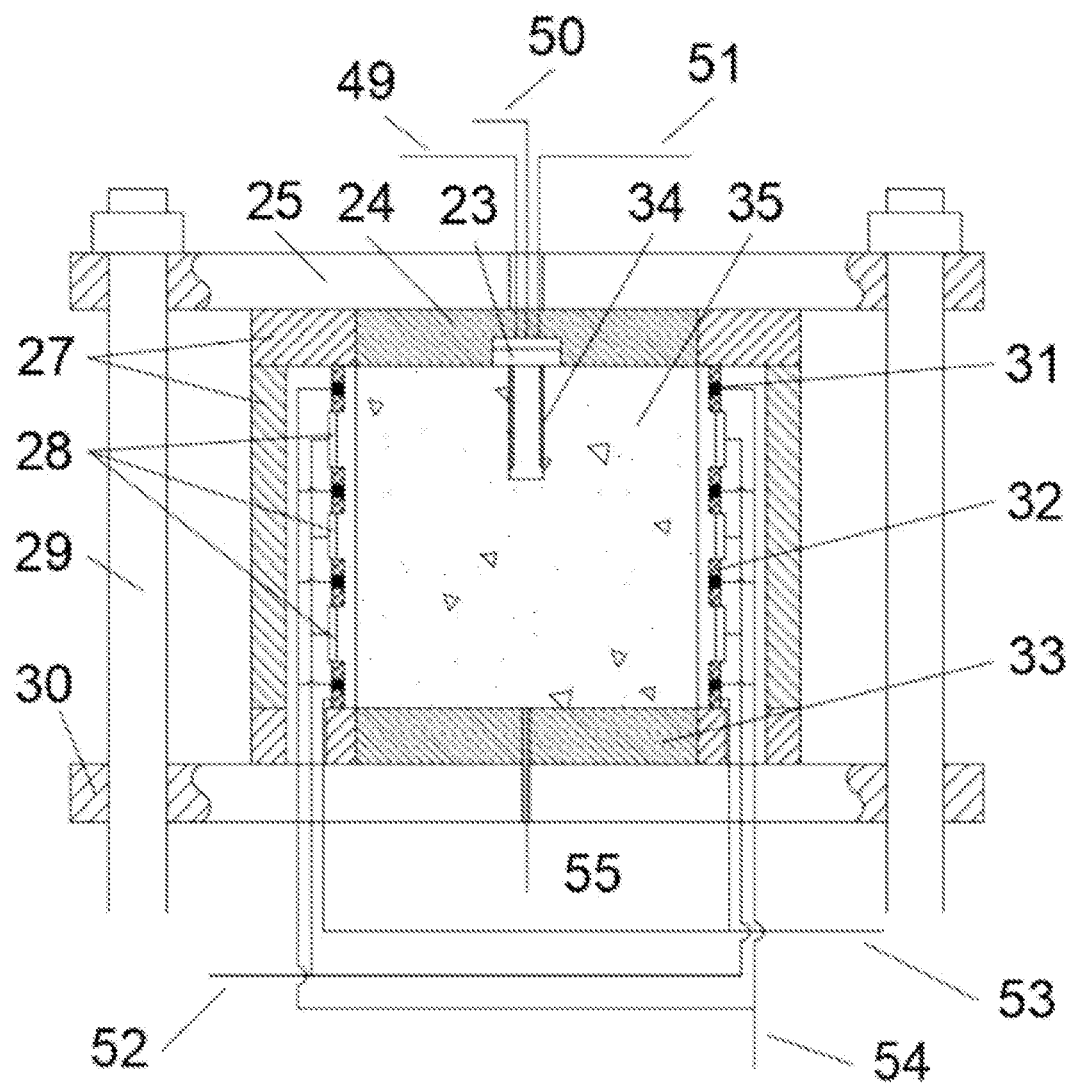
FIG. 2 is a structural schematic diagram of a fracturing system device in a preferred mode of execution of the present disclosure.

As shown in FIG. 1 and FIG. 2, in a preferred mode of execution of the present disclosure, the fracturing system III comprises a valve (d) 26, a test piece 35, a sealed wellhead 23 and a wellhole 34; the wellhole 34 is installed in a well hole, and holes are formed in the periphery of the wellhole 34 and used for simulating the fracturing process after perforation; and the sealed wellhead 23 is installed at a drill hole of the test piece 35, the sealed wellhead 23 is provided with a liquid inlet pipe, an oil inlet pipe and a recovery pipe, wherein the liquid inlet pipe is connected with the piston container (a) 6, the piston container (b) 7 and the piston container (c) 8, the oil inlet pipe is connected with the piston container (d) 9, the valve (d) 26 is installed at the liquid inlet pipe, and the recovery pipe is connected to a recovery system V.

Optionally, as shown in FIG. 1 and FIG. 2, a plurality of loading plates 28 are installed around the test piece 35 and connected to the large true triaxial loading servo supercharger 22 in the confining pressure loading system II for applying confining pressure to the test piece 35.

Figure 4:
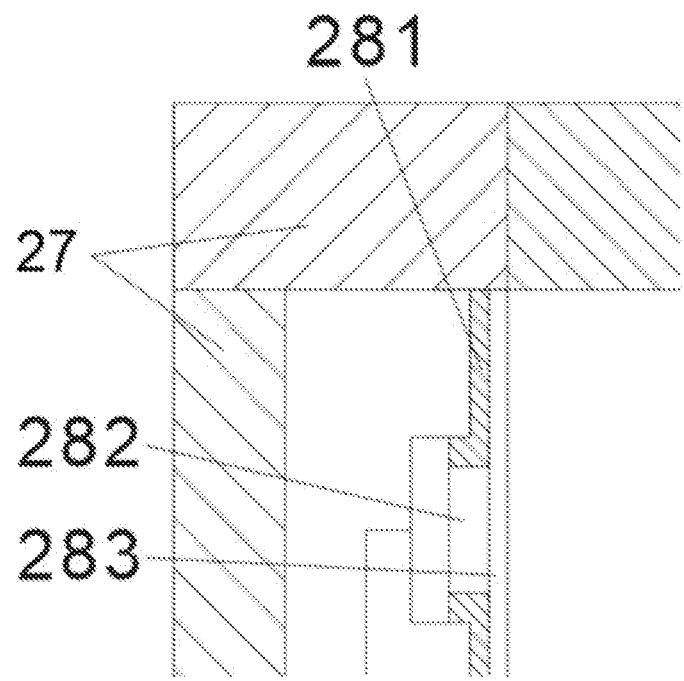
FIG. 4 is a schematic diagram of a test piece to which confining pressure is applied by a pressure plate in a preferred mode of execution of the present disclosure.

Specifically, as shown in FIG. 4, the loading plates 28 apply confining pressure to the test piece through hydraulic pistons 282, the outer sides of the hydraulic pistons 282 are fixed to sealing plates 27 through fixators 281, the hydraulic pistons 282 are controlled by the large true triaxial loading servo supercharger 22 to apply pressure to a pressure plate 283, the pressure plate 283 is in contact with a core, the area of the pressure plate 283 is the same as the side area of the core, and six hydraulic pistons 282 are used for applying pressure to the test piece, so that the purpose of controlling the confining pressure around the test piece is achieved.

Optionally, as shown in FIG. 1 and FIG. 2, acoustic emission probes 31 for monitoring the real-time damage condition of the test piece during fracturing are arranged around the test piece 35, the acoustic emission probes 31 are connected to a differential preamplifier group 37 to amplify the information monitored by the acoustic emission probes 31, and the preamplifier group 37 is connected to an acoustic emitter 36 to collect the information monitored by the acoustic emission probes 31.

Optionally, as shown in FIG. 1 and FIG. 2, warmers 32 are installed on the outer layer of the test piece and connected to a temperature controller 38 to be used for heating the test piece 35, so that the temperature condition of an actual reservoir is simulated, and the temperature of the test piece in the fracturing system III is kept constant.

Figure 3:
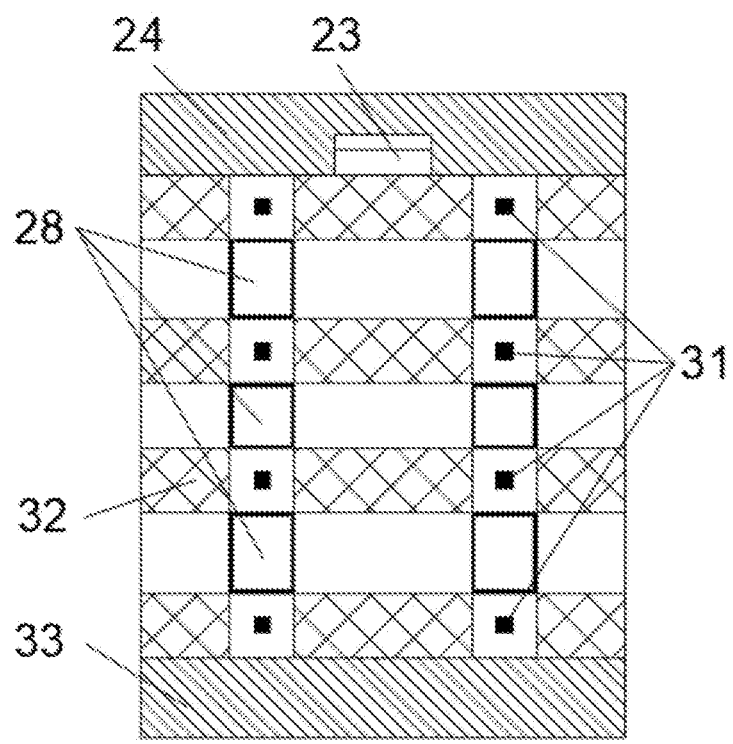
FIG. 3 is a structural schematic diagram of devices around a test piece in a preferred mode of execution of the present disclosure.

Referring to the structure as shown in FIG. 3, six loading plates 28, eight acoustic emission probes 31 and a plurality of warmers 32 are arranged around the test piece 35.

The fracturing system may be of a suitable structure, and in the mode of execution as shown in FIG. 1 and FIG. 2, the fracturing system comprises a top cover 25, an upper pressing plate 24, a lower pressing plate 33, and a base 30; after the monitoring equipment is installed on the test piece 35, the lower pressing plate 33 is connected to the bottom end of the test piece in a sealed mode and fixed to the base 30, and the upper pressing plate 24 and the top cover 25 are installed at the upper end of the test piece 35 in a sealed mode.

Optionally, the fracturing system III further comprises sealing plates 27 and stabilizers 29; the sealing plates 27 are installed around the test piece 35 fixed on the base 30 and the monitoring equipment in a sealed mode, the top cover 25, the base 30 and the middle part are fixed through four stabilizers 29 to be used for simulating an actual closed reservoir, the four stabilizers 29 are in contact with the bottom surface, and the cross sectional areas of the bottom ends of the stabilizers 29 are large, so that the contact area between the stabilizer and the ground is large, and a stable supporting effect is achieved.

Figure 5:
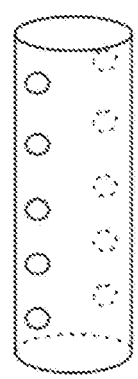
FIG. 5 is a schematic diagram of a wellhole with holes in a preferred mode of execution of the present disclosure.

Specifically, the fracturing system III comprises a sealed wellhead 23, an upper pressing plate 24, a top cover 25, a valve (e) 26, sealing plates 27, loading plates 28, stabilizers 29, a base 30, acoustic emission probes 31, warmers 32, a lower pressing plate 33, a wellhole with holes 34, a test piece 35, a microcomputer (c) 36, a differential preamplifier group 37 and a temperature controller 38. As shown in FIG. 2 and FIG. 3, the loading plates 28 are arranged around the test piece 35 and are externally connected with the large true triaxial loading servo supercharger 22 of the confining pressure loading system II, and the acoustic emission probes 31 and the warmers 32 are arranged around the test piece. The acoustic emission probes 31 and the warmers 32 are externally connected with the differential preamplifier group 37 and the temperature controller 38, respectively, wherein the temperature controller 38 has a temperature monitoring capability and is connected with the microcomputer (c) 36 so as to feed temperature back to the microcomputer (c) 36, the microcomputer (c) 36 can send an instruction to the temperature controller 38, and the temperature controller 38 can control the warmers 32 to perform corresponding actions according to the instruction so as to simulate the temperature condition of the actual reservoir and maintain the temperature of the test piece 35 in the fracturing system III to be constant. The sealed wellhead 23 is in sealing connection with the drill hole of the test piece, and the top cover 25, the upper pressing plate 24, the test piece 35, the lower pressing plate 33 and the base 30 are sequentially in sealing connection from top to bottom. The sealing plates 27 are fixed between the base 30 and the top cover 25 and surround around the test piece 35 to form a closed space. The top cover 25 and the base 30 are fixed through four stabilizers 29. Wherein, as shown in FIG. 5, two rows of through holes are formed in the wellhole with holes in the axial direction, and five through holes are formed in each row. However, the wellhole with holes is not limited to the specific structure, and the number of rows of the through holes and the number of the through holes can be selected according to actual requirements.

As shown in FIG. 2, the fracturing system III is connected to the piston container (d) 9 in the liquid supply system I through a pipeline (a) 49, is connected to the piston container 6 (a), the piston container (b) 7 and the piston container (c) 8 in the liquid supply system I through a pipeline (b) 50, is connected to a back pressure valve 45 in the recovery system V through a pipeline (c) 51, is connected to the large true triaxial loading servo supercharger 22 in the confining pressure loading system II through a pipeline (d) 52, is connected to the temperature controller 38 through a pipeline (e) 53, and is connected to the differential preamplifier group 37 through a pipeline (f) 54. Wherein the pipeline (a) 49 is an oil inlet pipe, the pipeline (b) 50 is a liquid inlet pipe, and the pipeline (c) 51 is a recovery pipe.

Energizing System IV

In a preferred mode of execution of the present disclosure, as shown in FIG. 1, the energizing system IV comprises a high-pressure energy storage tank 41 and a nitrogen cylinder 42; the upper portion of the high-pressure energy storage tank 41 is a constant-pressure medium, and the lower portion of the high-pressure energy storage tank 41 is energizing fluid; and the energizing fluid is fracturing liquid, and the constant-pressure medium is inert gas which can be nitrogen, helium and the like.

Wherein, the lower end of the high-pressure energy storage tank 41 is connected with the lower end of the fracturing system III, a far-end constant-pressure boundary condition is provided for the fracturing system III, surplus energy of fracturing liquid is stored in the fracturing process, and the stored energy is released in subsequent exploitation process, so that the purpose of simulating the fracturing synchronous energizing effect is achieved; and the upper end of the high-pressure energy storage tank 41 is connected with a pressure meter 40 for monitoring pressure provided by the energizing system, and the upper end of the high-pressure energy storage tank 41 is connected with the nitrogen cylinder 42. A valve (I) 401 is arranged between the nitrogen cylinder 42 and the high-pressure energy storage tank 41, and a valve (h) 391 used for being externally connected with a vacuum pump is arranged on a pipeline between the high-pressure energy storage tank 41 and the fracturing system.

The energizing system IV is formed by connecting a valve (f) 39, a valve (h) 391, a valve (I) 401, a high-pressure energy storage tank 41, a pressure meter (a) 40 and the nitrogen cylinder 42 in series through high pressure pipelines, and the high-pressure energy storage tank 41 in the energizing system IV is connected with the fracturing system III through a high pressure pipeline (g) 55.

Recovery System V

In a preferred mode of execution of the present disclosure, as shown in FIG. 1, the recovery system V comprises a back pressure valve 45, a surge tank 46, a back pressure pump 47 and an oil-water separation meter 48. The back pressure valve 45 is connected to the recovery pipe arranged on the sealed wellhead 23 of the fracturing system through a pipeline, and the oil-water separation meter 48 is connected to the back pressure valve 45 to collect, separate and meter liquid extracted from the fracturing system III; the back pressure pump 47 is connected with the back pressure valve 45 through the buffer tank 46 and used for controlling back pressure in the production process; and a valve (g) 43 and a pressure meter (b) 44 are arranged on a pipeline between the back pressure valve 45 and the recovery pipe of the fracturing system and used for monitoring the pressure of the recovery system V.

The recovery system V comprises a valve (g) 43, a pressure meter (b) 44, a back pressure valve 45, a buffer tank 46, a back pressure pump 47 and an oil-water separation meter 48. The oil-water separation meter 48 and the back pressure pump 47 are connected with the back pressure valve 45 and the buffer tank 46 through pipelines, respectively, and the buffer tank 46 is arranged at a left opening of the back pressure pump 47. The back pressure valve 45 and the valve (g) 43 are connected with the fracturing system III through high pressure pipelines, and the pressure meter (b) 44 is installed between the back pressure valve and the valve (g) 43. Wherein, the oil-water separation meter 48 can collect, separate and meter the liquid extracted from the fracturing system, and the back pressure pump 47 is connected to the back pressure valve 45 through the buffer tank 46 so as to control the bottom hole pressure during production, namely to simulate the bottom hole pressure during actual production.

It should be noted that in the preferred mode of execution of the present disclosure, a plurality of valves, three-way valves, high pressure pipelines and other components can be arranged in the shale oil fracturing synchronous energizing simulation experimental device according to needs.

In the second aspect, the present disclosure provides a usage method of the shale oil fracturing synchronous energizing simulation experimental device, and the method comprises the following steps:

a preparation stage: injecting crude oil into the test piece in a fracturing system III through a liquid supply system I so that the internal pressure of the fracturing system reaches a preset pressure P1, and recording the volume V1 of the injected crude oil; and heating a core to a preset temperature T1 through the warmer, and keeping the constant temperature for a period of time t1;

a fracturing stage: injecting fracturing liquid into the fracturing system III through a liquid supply system I for a fracturing experiment in which the injection time of the fracturing liquid is t2, and metering the volume V2 of the injected fracturing liquid, and keeping the confining pressure and the temperature of the fracturing system III constant over the period;

a soak stage: starting the energizing system IV so as to maintain the pressure of the fracturing system III at P1, maintaining the fracturing system III at the constant temperature T1 so that the experimental device is stabilized for a period of time t3 and the crude oil and the fracturing liquid in the test piece form a mixed fluid;

a recovery stage: opening the recovery system V, adjusting the recovery pressure P2 through the back pressure pump, and collecting the mixed fluid to the recovery system V to obtain primary extracted crude oil and fracturing liquid; metering the volume V3 of the primary extracted crude oil and the volume V4 of the extracted fracturing liquid; and an oil recovery agent huff-n-puff stage: closing the recovery system V, injecting the oil recovery agent into the fracturing system III by utilizing the liquid supply system I, until the pressure in the fracturing system III reaches P3 and the experimental device is stabilized for a period of time t4; opening the recovery system V, reducing the pressure of the fracturing system III to P4, and collecting liquid in the fracturing system III to the recovery system V; separating the extracted liquid to obtain secondary extracted crude oil and an oil recovery agent; and metering the volume V5 of the secondary extracted crude oil and the volume V6 of the oil recovery agent.

According to the volume V1 of the injected crude oil in the preparation stage, the volume V3 of the primary extracted crude oil in the recovery stage and the volume V5 of the secondary extracted crude oil in the oil recovery agent huff-n-puff stage, the recovery efficiency R1 of the fracturing synchronous energizing process and the recovery efficiency R2 of the oil recovery agent huff-n-puff stage are obtained, and the recovery efficiency of the reservoir depletion and oil recovery agent huff-n-puff processes after the fracturing synchronous energization are evaluated.

Wherein, the recovery efficiency R1 of the fracturing synchronous energizing process is equal to V3/V1*100%; and the recovery efficiency R2 of the oil recovery agent huff-n-puff stage is equal to V5/V1*100%.

According to the present disclosure, for better simulation of the exploitation of tight reservoir (shale oil reservoir) under the actual condition, preferably, the preparation stage of the core sample for a shale oil reservoir comprises the following preparation steps:

in order to perform a fracturing synchronous energizing experiment, enabling the prepared core to be cubic test piece;

after drilling the wellhole, performing a pre-heating experiment on the test piece, and measuring the time for well hole temperature to reach T1 through a temperature sensor to determine the heating time in the formal experiment process; and enabling a wellhole installed in a borehole is a wellhole with holes for simulating the perforation fracturing process in the real exploitation process.

It needs to be noted that the metering modes of the volume of the injected crude oil in the preparation stage, the volume of the fracturing liquid in the fracturing stage, the volume of the primary extracted crude oil and the volume of the extracted fracturing liquid in the recovery stage, the volume of the secondary extracted crude oil and the volume of the extracted oil recovery agent in the oil recovery agent huff-n-puff stage are conventional volume metering modes in the field. According to the present disclosure, the volumes of the pipelines can be measured to calibrate the measurement value of the volume.

Wherein, optionally, the method for injecting crude oil into the fracturing system in the preparation stage is an evacuated pressurized saturation method, and the volume of the injected crude oil is metered by the flow meter (d) 14.

By means of the method, in the fracturing stage, fracturing liquid enters through the liquid inlet pipe of the fracturing system III and fractures the test piece 35 under the high-pressure condition to form a complex fracture network, and surplus energy of the fracturing liquid is stored through the energizing system; and the fracturing liquid can be clean water, slickwater, guanidine gum fracturing liquid or foam fracturing liquid and the like.

In the soak stage, the fracturing liquid can displace crude oil saturated in the test sample through the imbibition effect, the mixed fluid of the fracturing liquid and the crude oil is extracted in the recovery stage, meanwhile, energy stored by the energizing system starts to be provided for the test piece, and the recovery effect is further improved.

In the recovery stage, in order to better simulate the variation characteristics of bottom hole pressure in the actual recovery process, optionally, the pressure drawdown mode of the recovery system in the recovery stage is constant-speed mode, namely, the recovery pressure P2 is adjusted through the back pressure pump.

In the oil recovery agent huff-n-puff stage, liquid injected into the fracturing system through the liquid supply system can be water or a chemical agent, the chemical agent can be a surfactant solution, an inorganic salt solution, a particle suspension or a combined liquid of different chemical agents, and the injection liquid of different components is mixed by controlling the flow rates of the piston container (b) 7 and the piston container (c) 8.

Wherein, in the method of the preferred mode of execution of the present disclosure, the pressure of each stage of the fracturing synchronous energizing experiment is collected in real time by the precise pressure sensor installed on a pipeline and pressure variations are recorded, and flow variations are collected and metered by the flow meters in real time.

In addition, parameters of the tight oil (shale oil) fracturing synchronous energizing simulation experimental method can be adjusted according to actual requirements. Preferably, in the preparation stage, the formation pressure P1 is 20-70 MPa, the constant temperature T1 is 40-150° C., and the stabilization time t1 is 15-30 days; in the fracturing stage, the fracturing liquid injection time t2 is 30-900 s; in the soak stage, the constant-temperature stabilization time t2 is 5-20 days; in the recovery stage and the oil recovery agent huff-n-puff stage, the recovery pressures P2 and P4 are set to be 5-20 MPa; and in the oil recovery agent huff-n-puff stage, the pressure P3 of the fracturing system is 15-50 MPa.

The method for evaluating the fracturing energization and the oil recovery agent huff-n-puff recovery efficiency is described in detail below through an embodiment by adopting the tight oil (shale oil) fracturing synchronous energizing simulation experimental device provided by the present disclosure, and the simulation experimental device adopted in each embodiment is as shown in FIG. 1.

Embodiment I

In the preparation stage, after a shale core test piece is prepared according to a conventional method, a hole is drilled along the axis of the core test piece. The core is installed in the fracturing system III, and horizontal stress of 20 MPa and vertical stress of 20 MPa are applied to the test piece through the confining pressure loading system II. The test piece is heated to 85° C. through the warmer 32 and the temperature controller 38, the temperature and the stress of the system are monitored through the temperature controller 38 and the large true triaxial loading servo supercharger 22, and the state is maintained for 30 min. The valve (h) 391 is externally connected with the vacuum pump, the valve (h) 391 is opened, the vacuum pump outside the valve (h) 391 is used for vacuumizing the test piece, meanwhile, the valve (c) 17 is opened, crude oil is injected into the fracturing system through the displacement pump (b) 5, the pressure variation of the precise pressure sensor (c) 171 is observed, and when the pressure reaches 1.2 times of the preset formation pressure 20 MPa, the displacement pump is closed for 1-2 days, so that the injected crude oil slowly permeates into the test piece; the process is repeated 5-7 times; when the displacement pump is closed for 2 days and the pressure displayed by the precise pressure sensor (c) 171 doesn't change, the vacuum pump is removed, crude oil is continuously injected into the fracturing system by using the displacement pump (b) 5 until crude oil flows out of the high pressure pipeline (g), the pump is stopped, and the saturated crude oil volume is recorded to be 1040 ml by the flow meter (d) 14.

In the fracturing stage, the valve (d) 17 is closed, and the valve (b) 15 and the valve (e) 26 are opened to inject fracturing liquid into the fracturing system to simulate the hydraulic fracturing process. Constant injection is maintained at the flow rate of 60 ml/min for 6 min through the pumping pressure system controller 2 and the hydraulic source servo valve 3, then the valve (b) 15 and the microcomputer (b) 19 are closed, the pressure shown by the precise pressure sensor (a) 151 is 34 MPa, and the volume of injected fracturing liquid is metered to be 360 ml through the flow meter 11. The valve (f) 39 is closed, the valve (I) 401 is opened, fracturing liquid and nitrogen are sequentially injected into the high-pressure energy storage tank 41, and when the pressure in the high-pressure energy storage tank 41 reaches 34 MPa, the valve (I) 401 is closed to keep the pressure of the high-pressure energy storage tank unchanged.

In the soak stage, the valve (f) 39 in the energizing system IV is opened, the constant temperature of the fracturing system III is kept at 85° C., and the experimental device is stabilized at the constant temperature for 3 days.

In the depletion exploitation stage, the valve (g) 43 of the recovery system V is opened, the back pressure pump 47 is adjusted to control the recovery pressure, the back pressure valve 45 is adjusted through the back pressure pump so that the recovery pressure is reduced to 10 MPa at a constant rate, the mixed fluid is collected to the oil-water separation meter 48, and the volume of primary extracted crude oil is 219.6 ml and the volume of extracted fracturing liquid is 154.3 ml after 0.3 hour of production.

Figure 6:
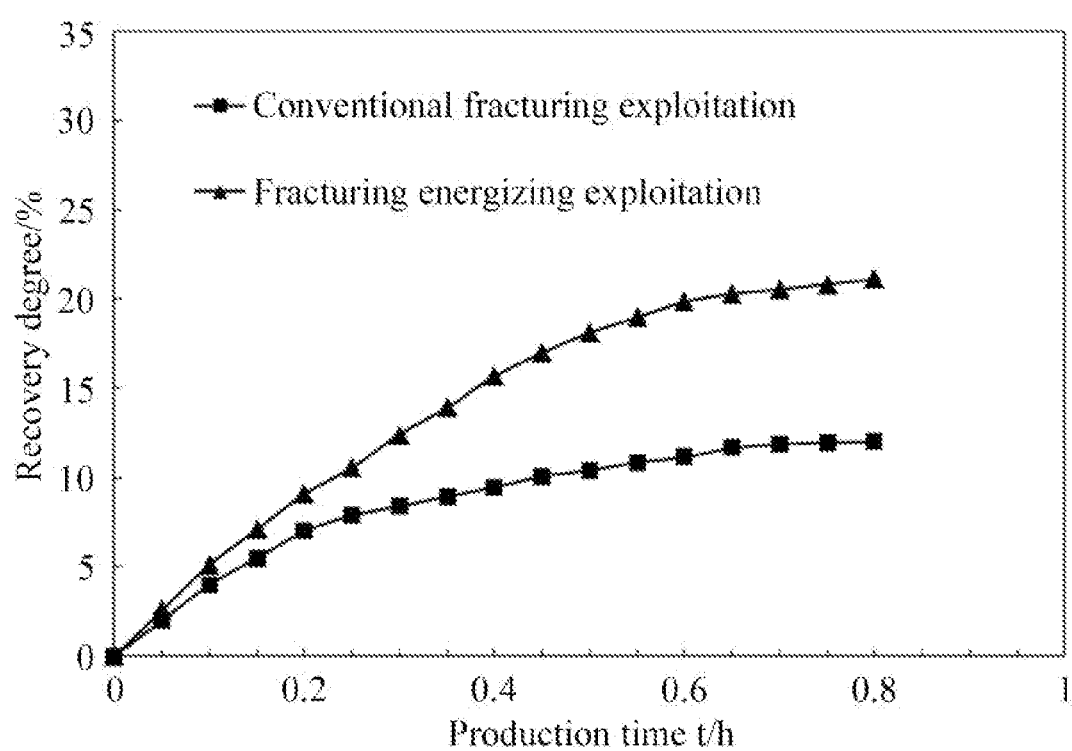
FIG. 6 is a recovery degree variation curve in the first embodiment of the present disclosure.
Figure 7:
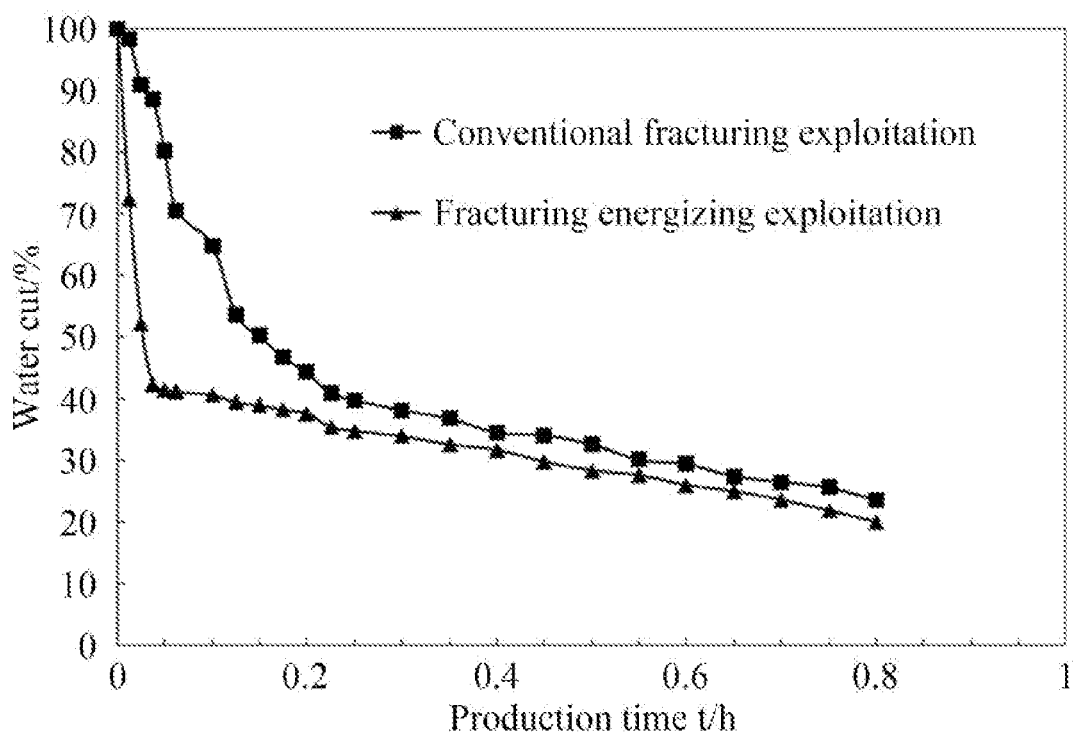
FIG. 7 is a water cut variation curve in the first embodiment of the present disclosure.

The results of the experiment are shown in FIG. 6 and FIG. 7. In FIG. 6, the recovery degree is the ratio of the volume of crude oil collected in the oil-water separation meter from the beginning of production to a certain time to the volume of crude oil injected. In FIG. 7, the water cut is the ratio of the volume of water collected in the oil-water separation meter to the total volume of liquid collected over a period of time. The final recovery degree of conventional fracturing (without considering the influence of fracturing synchronous energization) obtained in the experiment is 12.05%, and the recovery degree with considering the fracturing energization effect is 21.11%, which indicates that the fracturing synchronous energization technology can store redundant energy of fracturing liquid and effectively supplement the reservoir energy, so that the pressure drop of the reservoir is relieved, and the development effect of tight oil (shale oil) is effectively improved.

Embodiment II

In the preparation stage, after a shale core test piece is prepared according to a conventional method, a hole is drilled along the axis of the core test piece. The core is installed in the fracturing system III, and horizontal stress of 30 MPa and vertical stress of 30 MPa are applied to the test piece through the confining pressure loading system II. The test piece is heated to 90° C. through the temperature controller 38, the temperature and the stress of the system are monitored through the temperature controller 38 and the large true triaxial loading servo supercharger 22, and the state is maintained for 30 min. The valve (h) 391 is externally connected with the vacuum pump, the valve (h) 391 and the vacuum pump are opened for vacuumizing the test piece, meanwhile, the valve (c) 17 is opened, crude oil is injected into the fracturing system through the displacement pump (b) 5, the pressure change of the precise pressure sensor (c) 171 is observed, and when the pressure reaches 1.2 times of the preset strata pressure 30 MPa, the displacement pump is closed for 1-2 days, so that the injected crude oil slowly permeates into the test piece; the process is repeated 5-7 times; when the displacement pump is closed for 2 days and the pressure value displayed by the precise pressure sensor (c) 171 is basically unchanged, the vacuum pump is removed, crude oil is continuously injected into the fracturing system by using the displacement pump (b) 5 until crude oil is about to flow out of the high pressure pipeline (g), the pump is stopped, and the saturated crude oil volume is recorded to be 983.5 ml by the flow meter (d) 14.

In the fracturing stage, the valve (d) 17 is closed, and the valve (b) 15 and the valve (e) 26 are opened to inject fracturing liquid into the fracturing system to simulate the hydraulic fracturing process. After the injection pressure of the fracturing liquid is adjusted to be 50 MPa and constant-pressure injection is maintained for 20 min through the pumping pressure system controller 2 and the hydraulic source servo valve 3, the valve (b) 15 and the microcomputer (b) 19 are closed, the pressure is read to be 45 MPa through the precise pressure sensor (a) 151, and the volume of injected fracturing liquid is metered to be 285.4 ml through the flow meter 11. The valve (f) 39 is closed, the valve (I) 401 is opened, formation water and nitrogen are sequentially injected into the high-pressure energy storage tank 41, and when the pressure in the high-pressure energy storage tank 41 reaches 45 MPa, the valve (I) 401 is closed to keep the pressure of the high-pressure energy storage tank unchanged.

In the soak stage, the valve (f) 39 in the energizing system IV is opened, the constant temperature of the fracturing system III is kept at 90° C., and the experimental device is stabilized at the constant temperature for 5 days.

In the depletion exploitation stage, the valve (g) 43 of the recovery system V is opened, the back pressure pump 47 is adjusted to control the recovery pressure, and the back pressure valve is adjusted through the back pressure pump so that the recovery pressure is reduced to 15 MPa for production for 0.3 h. The mixed fluid is collected to the oil-water separation meter 48 in the production process, and the volume of primary extracted crude oil is 176.6 ml and the volume of extracted fracturing liquid and simulation formation water is 102.8 ml.

In the huff stage, the valve (g) 43 in the recovery system V and the valve (f) 39 in the energizing system IV are closed, the three-way valve 18 of the liquid supply system I is adjusted so that displacement pump (a) 4 displaces the piston container (b) 7 and the piston container (c) 8, the surfactant solution is injected into the fracturing system III until the pressure displayed by the precise pressure sensor (b) 161 is 30 MPa, then the surfactant solution is injected into the fracturing system at a constant rate for 0.2 h, and the volume of the injected surfactant solution is metered by the flow meter (c) 13 and the flow meter (d) 14 to be 120.0 ml.

In the soak stage, the constant temperature of 90° C. is kept for 5 days.

In the puff stage, the valve (g) 43 of the recovery system is opened, the back pressure pump 47 is adjusted to control the recovery pressure, the back pressure valve 45 is adjusted through the back pressure pump so that the recovery pressure is reduced to 15 MPa at a constant rate, the mixed fluid is collected to the oil-water separation meter 48, and the volume of secondary extracted crude oil is 84.5 ml and the volume of extracted water is 67.9 ml.

Figure 8:
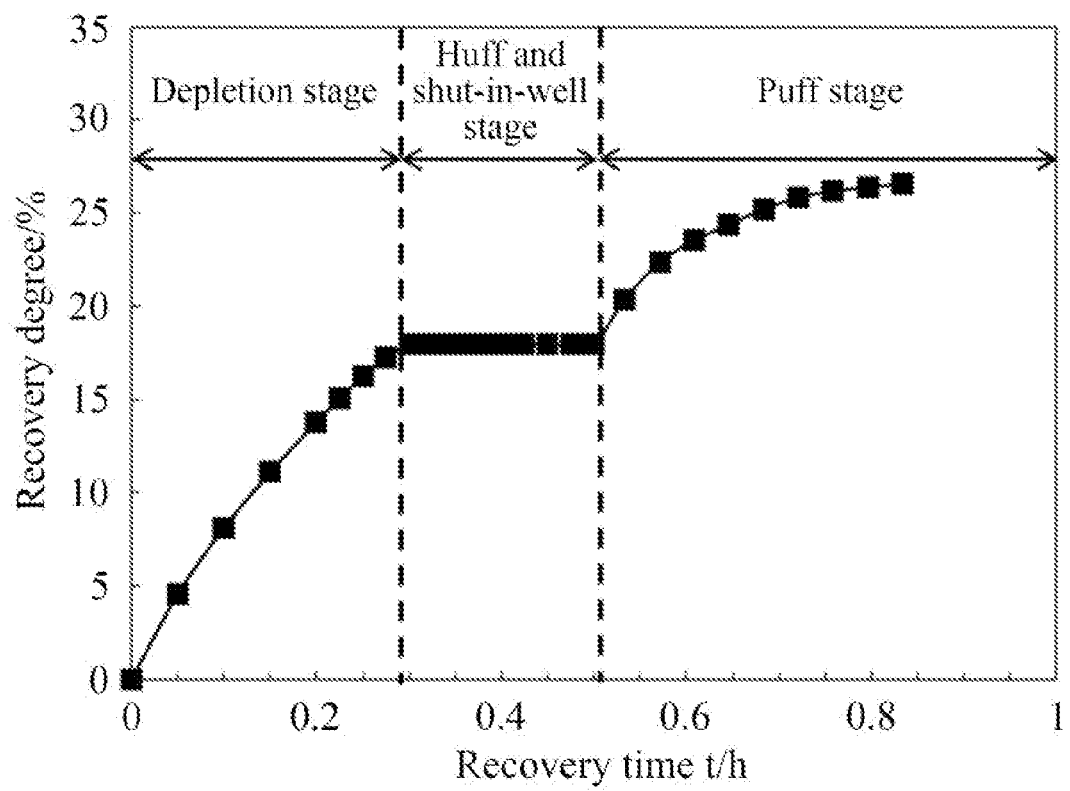
FIG. 8 is a recovery degree variation curve in the second embodiment of the present disclosure.
Figure 9:
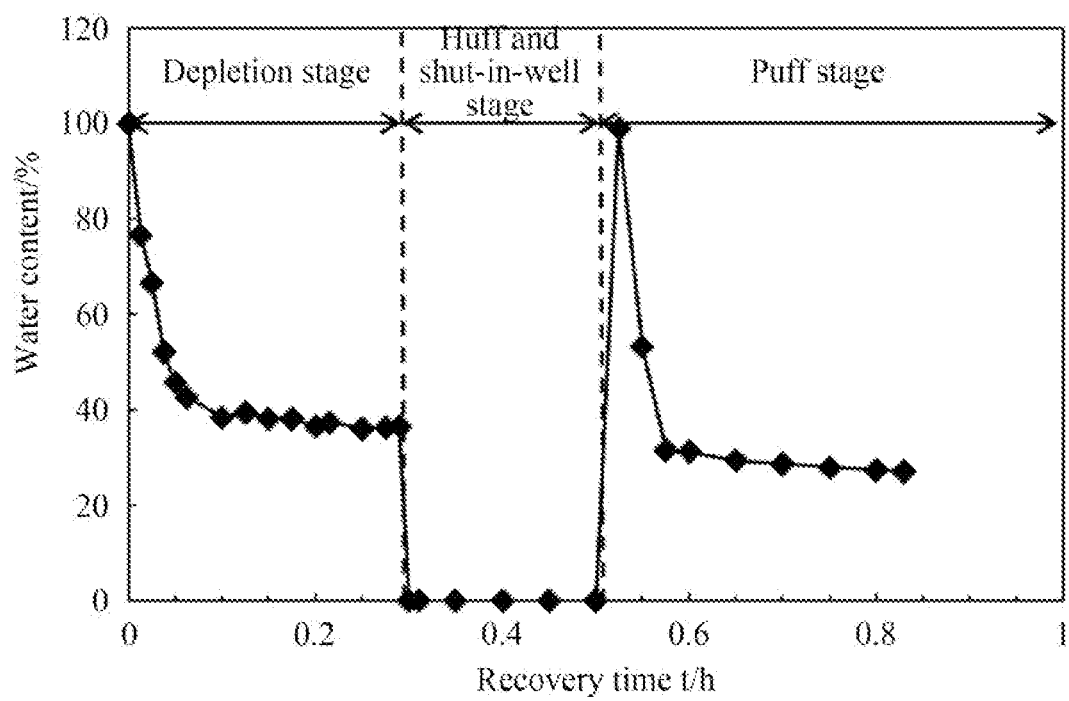
FIG. 9 is a water cut variation curve in the second embodiment of the present disclosure.

The results of the experiment are shown in FIG. 8 and FIG. 9. In FIG. 8, the recovery degree is the ratio of the volume of crude oil collected in the oil-water separation meter from the beginning of production to a certain time to the volume of crude oil injected. In the experiment process, the recovery degree in the depletion exploitation stage after fracturing is measured to be 17.96%, the recovery degree reaches 26.55% after surfactant solution huff and puff measures are taken, and the recovery efficiency increment is 8.59%. In FIG. 9, the water cut is the ratio of the volume of collected water in the oil-water separation meter to the total volume of collected liquid during a certain period of time, the water cut first drops rapidly during reservoir depletion stage, then the drop is slowed down, no water is produced in the huff and soak stages, the initial water production in the puff stage is higher due to the injection of water, and the water cut in the later puff stage is reduced to 27.16%. Therefore, in the shale oil exploitation process, after fracturing synchronous energization, the recovery efficiency can be further improved by injecting the oil recovery agent such as the surfactant solution.

By utilizing the experimental device provided by the present disclosure, integrated simulation of shale oil fracturing and exploitation can be realized, fracturing synchronous energization and simulations of subsequent depletion and oil recovery agent huff-n-puff are realized through the same set of experimental device, and the recovery efficiencies of different exploitation modes are evaluated. Fractures on a sample are obtained by actual fracturing during the simulation of the exploitation process instead of being manually set, so that the actual conditions of a reservoir can be simulated more accurately, and effective means is provided for the technical research on the fracturing synchronous energizing mechanism and the enhanced recovery of an unconventional oil reservoir; and in addition, by utilizing the experimental device provided by the present disclosure, the fracturing synchronous energizing process of the shale oil under a real reservoir condition can be simulated. In the fracturing process, redundant energy of fracturing liquid is stored through the energizing system and released in the subsequent production process, the attenuation speed of the pressure of the test piece is reduced, and the fracturing synchronous energizing effect is effectively embodied.

The preferred modes of execution of the present disclosure are described above with reference to the attached figures, but the present disclosure is not limited to the foregoing modes of execution. Within the scope of the technical idea of the present disclosure, multiple simple modifications can be made to the technical solution of the present disclosure. Individual specific technical features are included in combination in any suitable manner. In order to avoid unnecessary repetition, various possible combinations of the present disclosure are not otherwise described. However, such simple modifications and combinations should also be considered as disclosed herein, all falling within the scope of the present disclosure.

What is claimed is:

1. A shale oil fracturing synchronous energizing simulation experimental device, comprising a liquid supply system, a confining pressure loading system, a fracturing system, an energizing system and a recovery system, wherein the liquid supply system is used for storing fluid and can inject the fluid into the fracturing system;

the fracturing system comprises a plurality of loading plates installed around a test piece and connected to a large true triaxial loading servo supercharger in the confining pressure loading system (II) for applying confining pressure to the test piece; the fracturing system can bear the test piece, the fracturing system is used for simulating a rock medium of a tight reservoir and boundary conditions around the rock medium, receives the fluid injected by the liquid supply system and serves as a seepage space of the fluid, and the fracturing system is configured to be capable of maintaining own temperature; the loading plate comprises a hydraulic piston, a fixator and a pressure plate, and the pressure plate is connected with the test piece;

the confining pressure loading system is connected with the fracturing system and used for providing simulated confining pressure for the test piece, and the confining pressure loading system can maintain stable stress conditions in the horizontal and vertical directions for the test piece;

the energizing system is connected with the fracturing system and used for simulating an energy supplementing effect on a formation after fracturing liquid is injected; and the recovery system is used for collecting liquid discharged from the fracturing system, and the recovery system can control the pressure of the fracturing system (III) and separate and meter the discharged liquid;

the confining pressure loading system comprises the large true triaxial loading servo supercharger, a true triaxial loading instrument hydraulic source and a true triaxial loading instrument controller, the true triaxial loading instrument hydraulic source is in fluid connection with the large true triaxial loading servo supercharger so as to provide a hydraulic source for the large true triaxial loading servo supercharger;

the true triaxial loading instrument controller is connected with the large true triaxial loading servo supercharger;

the large true triaxial loading servo supercharger is connected with the loading plates so as to provide confining pressure for the test piece; and the energizing system comprises a high-pressure energy storage tank, the high-pressure energy storage tank is filled with a constant-pressure medium located on an upper portion and an energizing fluid located on the lower portion, and a lower portion of the high-pressure energy storage tank is connected with the fracturing system so as to simulate an energizing effect after fracturing liquid is injected.

2. The shale oil fracturing synchronous energizing simulation experimental device according to claim 1, wherein the liquid supply system comprises a plurality of liquid storage containers, the liquid storage containers are respectively used for storing different types of fluids, and the fluids in the liquid storage containers communicate with the fracturing system.

3. The shale oil fracturing synchronous energizing simulation experimental device according to claim 2, wherein at least one of the liquid storage containers is configured to be capable of controlling the internal pressure of the liquid storage container, and a flow meter is arranged on a pipeline between the liquid supply system and the fracturing system.

4. The shale oil fracturing synchronous energizing simulation experimental device according to claim 1, wherein the fracturing system comprises movable loading plates, the loading plates are arranged around the test piece, and the confining pressure loading system is connected with the loading plates so as to provide confining pressure for the test piece.

5. The shale oil fracturing synchronous energizing simulation experimental device according to claim 1, wherein the test piece is a core sample for a shale oil reservoir, and the core sample for a shale oil reservoir is arranged in the fracturing system so as to simulate a shale medium of a shale oil reservoir and boundary conditions around the shale medium of the shale oil reservoir.

6. The shale oil fracturing synchronous energizing simulation experimental device according to claim 1, wherein the fracturing system comprises warmers and acoustic emission probes, the warmers are connected with the test piece so as to control the temperature of the test piece, and the acoustic emission probes are arranged around the test piece so as to monitor a damage condition of the test piece.

7. The shale oil fracturing synchronous energizing simulation experimental device according to claim 1, wherein the recovery system comprises a back pressure valve, a back pressure pump, a buffer tank and an oil-water separation meter, the back pressure valve is connected with the output end of the fracturing system, and the oil-water separation meter is connected with the back pressure valve so as to collect, separate and meter liquid extracted from the fracturing system; and the back pressure pump is connected with the back pressure valve through the buffer tank so as to control bottom hole pressure in a production process.

8. A shale oil fracturing synchronous energizing simulation experimental method, wherein the method uses the shale oil fracturing synchronous energizing simulation experimental device according to claim 1, and the method comprises the following steps:

a preparation stage: injecting crude oil into the test piece in a fracturing system so that the internal pressure of the fracturing system reaches a first preset pressure (P1), and recording a first volume (VI) of the injected crude oil; heating a core sample for a shale oil reservoir for simulating a shale medium of a shale oil reservoir and boundary conditions around the shale medium of the shale oil reservoir to a preset temperature (T1), and stabilizing the test piece for a first period of time (t1);

a fracturing stage: injecting fracturing liquid into the fracturing system through a liquid supply system for a fracturing experiment in which the injection time of the fracturing liquid is a second period of time (t2), and metering a second volume (V2) of the injected fracturing liquid;

a soak stage: starting the energizing system so as to maintain the pressure of the fracturing system at the first preset pressure (P1), maintaining the fracturing system at the preset temperature (T1) so that the shale oil fracturing synchronous energizing simulation experimental device is stabilized for a third period of time (t3) and the crude oil and the fracturing liquid in the test piece form a mixed fluid;

a recovery stage: controlling the pressure of the fracturing system to be a second preset pressure (P2) through the recovery system, and separating and metering the mixed fluid through the recovery system to obtain primary extracted crude oil and fracturing liquid; metering a third volume (V3) of the primary extracted crude oil and a fourth volume (V4) of the extracted fracturing liquid; and an oil recovery agent huff-n-puff stage: closing the recovery system, injecting the oil recovery agent into the fracturing system by utilizing the liquid supply system, performing oil recovery agent huff and puff so that the pressure in the fracturing system reaches a third preset pressure (P3) and the shale oil fracturing synchronous energizing simulation experimental device is stabilized for a fourth period of time (t4); opening the recovery system, reducing the pressure of the fracturing system to a fourth preset pressure (P4), and collecting liquid in the fracturing system to the recovery system; separating an extracted liquid through the recovery system to obtain secondary extracted crude oil and an oil recovery agent; and metering a fifth volume (V5) of the secondary extracted crude oil and a sixth volume (V6) of the oil recovery agent.

9. The method according to claim 8, wherein the core sample for a shale oil reservoir is a cubic test piece, a wellhole installed in a borehole is a wellhole with holes and used for simulating a perforation fracturing process in a real exploitation process, and a preparation stage of the core sample for a shale oil reservoir comprises a following preparation steps:

after drilling the wellhole, performing a pre-heating experiment on the test piece, and measuring the time for well hole temperature to reach T1 through a temperature sensor to determine the heating time in a formal experiment process.

10. The method according to claim 8, wherein

P1 is greater than or equal to 20 MPa and less than or equal to 70 MPa, T1 is greater than or equal to 40° C. and less than or equal to 150° C., and t1 is greater than or equal to 15 days and less than or equal to 30 days;

t2 is greater than or equal to 30 s and less than or equal to 900 s;

P2 and P4 are equal and are greater than or equal to 5 MPa and less than or equal to 20 MPa; and P3 is greater than or equal to 15 MPa and less than or equal to 50 MPa.

11. The method according to claim 8, wherein the liquid supply system comprises a plurality of liquid storage containers, the liquid storage containers are respectively used for storing different types of fluids, and the fluids in the liquid storage containers communicate with the fracturing system.

12. The method according to claim 11, wherein at least one of the liquid storage containers is configured to be capable of controlling the internal pressure of the liquid storage container, and a flow meter is arranged on a pipeline between the liquid supply system and the fracturing system.

13. The method according to claim 8, wherein the fracturing system comprises movable loading plates, the loading plates are arranged around the test piece, and the confining pressure loading system is connected with the loading plates so as to provide confining pressure for the test piece.

14. The method according to claim 8, wherein the test piece is a core sample for a shale oil reservoir, and the core sample for a shale oil reservoir is arranged in the fracturing system so as to simulate a shale medium of a shale oil reservoir and boundary conditions around the shale medium of the shale oil reservoir.

15. The method according to claim 8, wherein the fracturing system comprises warmers and acoustic emission probes, the warmers are connected with the test piece so as to control the temperature of the test piece, and the acoustic emission probes are arranged around the test piece so as to monitor a damage condition of the test piece.

16. The method according to claim 8, wherein the recovery system comprises a back pressure valve, a back pressure pump, a buffer tank and an oil-water separation meter, the back pressure valve is connected with the output end of the fracturing system, and the oil-water separation meter is connected with the back pressure valve so as to collect, separate and meter liquid extracted from the fracturing system; and the back pressure pump is connected with the back pressure valve through the buffer tank so as to control bottom hole pressure in a production process.

* * * * *